(12) United States Patent
Munaro

(10) Patent No.: US 9,155,856 B2
(45) Date of Patent: Oct. 13, 2015

(54) TRACHEOTOMY DEVICE

(75) Inventor: Marco Munaro, Castronno (IT)

(73) Assignee: GIMAC DI MACCAGNAN GIORGIO, Castronno (IT)

( * ) Notice: Subject to any disclaimer, the term of this patent is extended or adjusted under 35 U.S.C. 154(b) by 52 days.

(21) Appl. No.: 13/992,117

(22) PCT Filed: Dec. 5, 2011

(86) PCT No.: PCT/IB2011/055448
§ 371 (c)(1),
(2), (4) Date: Jun. 6, 2013

(87) PCT Pub. No.: WO2012/080897
PCT Pub. Date: Jun. 21, 2012

(65) Prior Publication Data
US 2013/0261393 A1    Oct. 3, 2013

(30) Foreign Application Priority Data
Dec. 14, 2010   (EP) ..................................... 10425381

(51) Int. Cl.
*A61M 16/00* (2006.01)
*A61M 16/04* (2006.01)
*A61B 1/267* (2006.01)

(52) U.S. Cl.
CPC ............ *A61M 16/0488* (2013.01); *A61B 1/267* (2013.01); *A61M 16/0472* (2013.01); *A61M 16/0434* (2013.01)

(58) Field of Classification Search
CPC ..................... A61M 16/0488; A61M 16/0434; A61M 16/0472; A61B 1/267
USPC ........... 128/200.26, 207.14, 207.29; 600/114, 600/120, 124; 604/43, 44, 158, 164.05, 604/523, 524
See application file for complete search history.

(56) References Cited

U.S. PATENT DOCUMENTS

| | | | | |
|---|---|---|---|---|
| 5,104,388 | A * | 4/1992 | Quackenbush | ............... 604/264 |
| 5,797,882 | A * | 8/1998 | Purdy et al. | ............. 604/164.09 |
| 6,637,435 | B2 * | 10/2003 | Ciaglia et al. | ............ 128/207.29 |
| 6,706,017 | B1 * | 3/2004 | Dulguerov | ............... 604/164.01 |
| 7,036,510 | B2 * | 5/2006 | Zgoda et al. | ............. 128/207.29 |
| 7,762,949 | B2 * | 7/2010 | Nakao | ............................ 600/153 |
| 2006/0124134 | A1 * | 6/2006 | Wood | ........................ 128/207.29 |
| 2010/0224186 | A1 * | 9/2010 | Uesugi | ..................... 128/200.26 |

FOREIGN PATENT DOCUMENTS

| | | |
|---|---|---|
| CA | 2 191 199 C | 11/1995 |
| WO | 02/20077 A1 | 3/2002 |

* cited by examiner

*Primary Examiner* — Justine Yu
*Assistant Examiner* — Douglas Sul
(74) *Attorney, Agent, or Firm* — Pearne & Gordon LLP

(57) ABSTRACT

A tracheotomy device with a disposable flexible sheath furnished with a main channel for insertion of a support carrying endoscopic surgical instruments insertable in a trachea and a secondary channel for insertion of a perforation needle. The sheath has a spout curved in the perforating direction or susceptible of bending and configured as a dilator body having tapered shape so as to enter the hole formed in the trachea and to progressively dilate it.

14 Claims, 3 Drawing Sheets

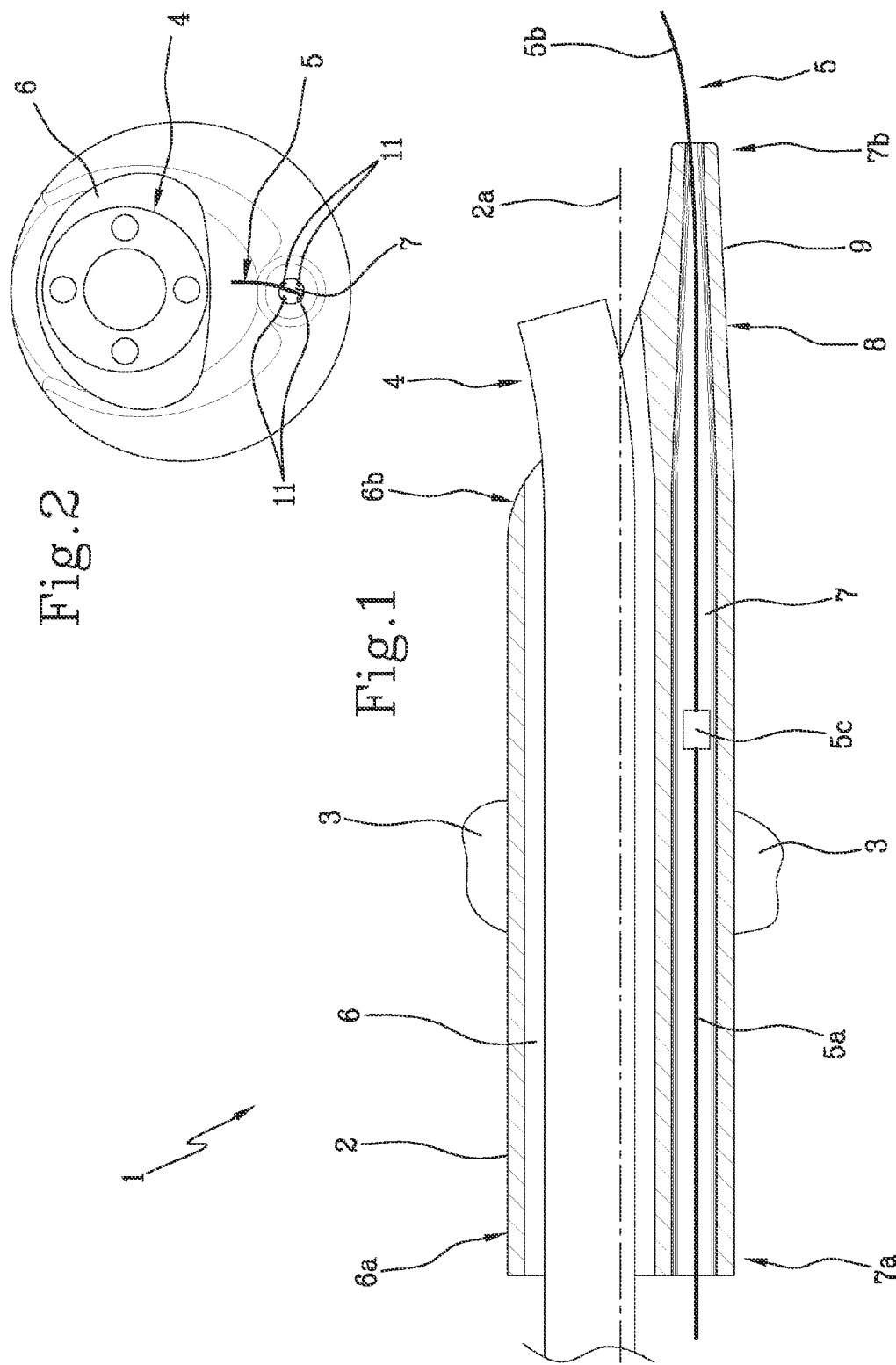

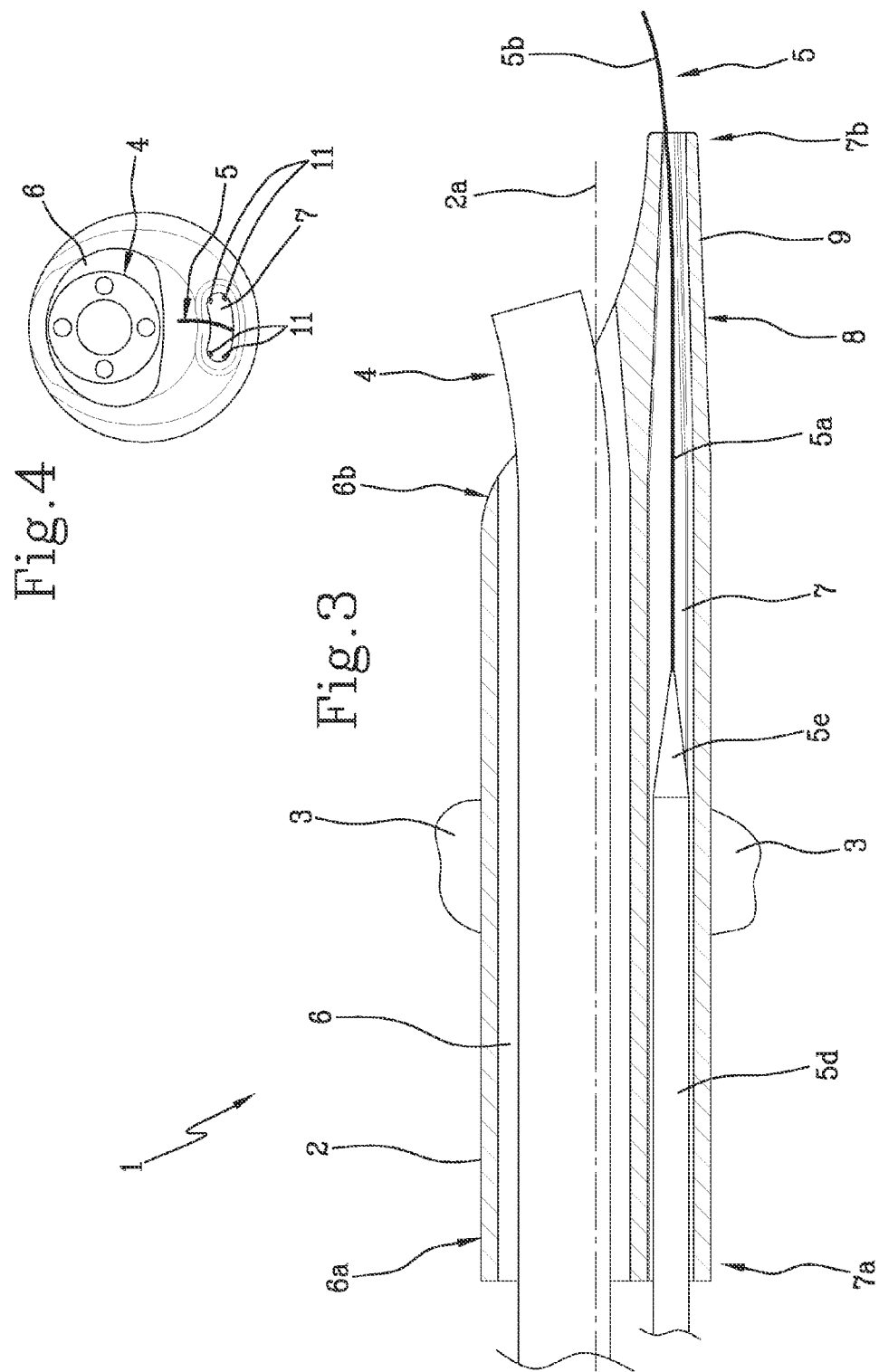

TRACHEOTOMY DEVICE

The present invention relates to a percutaneous tracheotomy/tracheostomy device.

In the intensive care units (ICUs) the endotracheal intubation is the main method for assistance and control of the respiratory airways, but only for limited periods of time. In fact, introduction of a endotracheal tube, even for short periods of time, can cause damages to the larynx and trachea structures that however can be spontaneously solved within a few days.

The case is different when intubation must necessarily be extended for prolonged periods of time or in case of high airways obstruction, maxillofacial traumas, pulmonary infections and others. In these case a percutaneous dilation tracheotomy/tracheostomy (PDT) is necessary.

Up to now there are many techniques suitable to carry out tracheostomies which involve a trachea perforation and subsequent dilation of the stoma, with different manoeuvres involving use of several surgical instruments. Perforation always takes place from the outside to the inside, which sometimes can give rise to dangerous consequences, while dilation can take place from the outside to the inside or, vice versa, from the inside to the outside.

Generally perforation takes place by introducing an endoscope through the patient's mouth until reaching the trachea, which endoscope is provided with an optical probe and a lighting device enabling the inner region of the trachea to be inspected and trans-illuminated so as to identify the intra-ring space into which the cannula needle is to be fitted from the outside to the inside. Therefore, the lighting device acts as a lighted target showing the operator the exact point where the incision is to be made. Once the stoma has been formed, the different techniques contemplate different dilation methods and different methods of positioning the ventilation cannula.

For instance, one technique involves introduction of a metal wire into the cannula needle to the other end of which a dilator cone is connected. The wire is pushed into the cannula needle, is caused to rise along the tracheoscope and finally, once it has emerged from the mouth and has been disengaged from the tracheoscope, is connected to a dilator cone. By subsequently pulling the wire that is at the outside of the hole made in the patient's neck, the cone is dragged along inside the trachea until it comes out thereof, from the inside to the outside, thus producing the desired dilation. This dilator cone is incorporated into a ventilation cannula and, once it has come out of the skin, it is cut and separated from the cannula which through a manoeuvre involving a 180° rotation is correctly positioned in the tracheal tree and connected to the ventilator.

Other techniques contemplate use of a curved dilator clamp provided with a groove enabling the guide wire introduced after the starting perforation to slide therethrough or utilise a threaded cone-shaped element that is "screwed" in the trachea.

The techniques presently used all have the same risks for the patient, in particular during the perforation step, such as a potential breaking of the tracheal rings, injuries to the glottis or the rear trachea wall, tracheal stenosis, symptomatic partial occlusion, possible tracheo-esophageal fistulas, bleeding, infection risks or risks of a "false way" so that the cannula is guided into the subcutaneous tissue instead of being guided into the trachea.

Other drawbacks of the presently known techniques are for example represented by the great fragility of the optical instruments and the constant requirement of sterilising all surgical instruments. The endoscope, for instance, must be constantly sterilised but the internal instruments thereof can make this operation delicate.

Other techniques contemplate manoeuvres causing repeated intubations and extubations of the patient to enable placement of the respiratory tube and therefore, in addition to the continuous friction of the trachea's inner walls with surgical instruments, a long time for the operation is required, which makes these manoeuvres complicated and long.

In this context, the technical task underlying the present invention is to propose a device for tracheotomies overcoming the above mentioned drawbacks of the known art.

In particular, it is an aim of the present invention to make available a device for tracheotomies capable of avoiding damages to the patient during perforation of the trachea.

Note that it is also an aim of the present invention to conceive a device capable of enabling execution of the tracheotomy operation in the direction "from the inside to the outside" (in opposition to the devices of known type instead operating "from the outside to the inside") so that the risks of infections and the so called "false ways" are limited.

Another aim of the present invention is to propose a device for tracheotomies enabling a tracheotomy to be executed in an easy and quick manner which is as less as possible traumatic for the patient.

Finally, it is a further aim of the invention to propose a device for tracheotomies making the preparatory steps of the instruments required for the operation easier and allowing a simpler use of the most delicate instruments, reducing the sterilisation requirements when possible.

The technical task mentioned and the aims specified are substantially achieved by a device for tracheotomy comprising the technical features set out in one or more of the appended claims.

Further features and advantages of the present invention will become more apparent from the non-limiting description of a preferred but not exclusive embodiment of a device for tracheotomy as illustrated in the accompanying drawings, in which:

FIG. 1 is a sectional side view of the tracheotomy device being the object of the invention, in a first embodiment;

FIG. 2 is a plan view of the device seen in FIG. 1;

FIG. 3 is a sectional side view of the tracheotomy device being the object of the invention, in a second embodiment;

FIG. 4 is a plan view of the device seen in FIG. 3;

Figure 5:
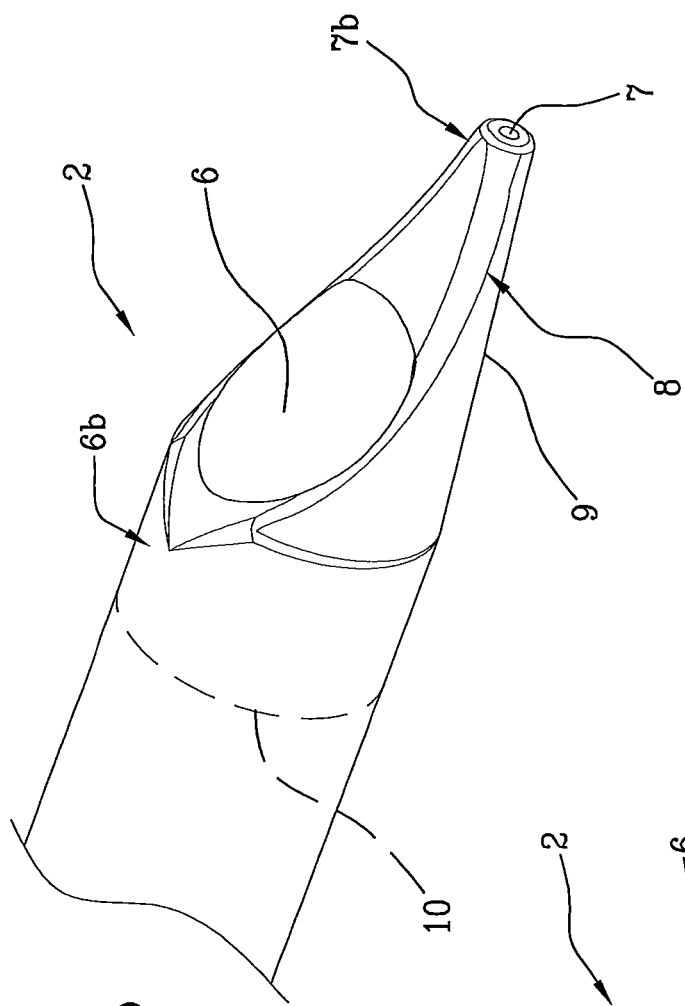
FIG. 5 is a perspective view of a portion of the device in FIG. 1, with a first example of a construction detail.

Referring particularly to the accompanying drawings, a tracheotomy device in accordance with the present invention has been generally identified by reference numeral 1. As shown in FIGS. 1 and 3, the device 1 comprises a disposable flexible sheath 2 to be put on fitting means 4 carrying surgical endoscopic instruments insertable into a trachea, such as en endoscope, a fibroscope or a tracheoscope, for example. The fitting means 4 must compulsorily comprise at least one optical probe for inspecting the operation area, a light source and a lumen or ventilation channel, coaxial with the axis of said fitting means.

The fitting means 4 can also have other channels through which washing and/or suction operations both on the inner walls of the trachea and the instruments in use can be carried out.

Sheath 2 can be advantageously made of anallergic plastic material, which is elastic to some extent so that it can suit the sizes of the fitting means 4, but also has a certain degree of stiffness so as to correctly guide and route a perforation element 5 along the trachea until the perforation point.

Sheath 2 has a major longitudinal extension size along an axis 2a and comprises a plurality of channels extending parallel to axis 2a. In particular, sheath 2 comprises at least one main channel 6 for introduction of said fitting means 4, and at least one secondary channel 7 for guiding the perforation element 5 slidably insertable into said channel.

The secondary channel 7 disposed in side by side relationship with the main channel 6, has a longitudinal extension greater than that of the main channel 6. In addition, the secondary channel 7 has stiffening ribs 11 distributed along its longitudinal extension which counteract possible deviations of the perforation element 5 from its travel internally of the secondary channel 7 and also bear possible combined bending and compressive stresses from the perforation element 5.

The main channel 6 and secondary channel 7 both have a first end 6a, 7a that is open and through which the fitting means 4 carrying the endoscopic instruments and the perforation element are respectively inserted, and a second end 6b, 7b that is open as well and through which the fitting means 4 carrying the endoscopic instruments and the perforation element 5 respectively emerge.

In an alternative embodiment of sheath 2, not shown, the main channel 6 has a second end 6b that is closed but provided with a transparent window, through which the light source can illuminate the region to be operated and the optical probe can carry out a clear and definite inspection.

Externally, around the side walls, sheath 2 can have an inflatable casing or pouch 3.

The device 1 also comprises guide and pointing means 8 adapted to guide the perforation element 5 in the perforation direction and address and position it in the correct region to be operated.

This guide and pointing means 8 comprises a spout 9 located at the second end 7b of the secondary channel 7. In particular, spout 9 is the exceeding portion of the secondary channel 7 with respect to the main channel 6. Preferably, spout 9 is curved or has a varying and modifiable bending degree or curvature based on requirements. The curvature of spout 9 has a concavity facing the longitudinal axis 2a of sheath 2. This curvature can be preformed using particular materials capable of maintaining the desired shape, or can be obtained in case of need through bending-controlling means.

If the curvature is to be obtained in case of need, it is possible for example (although not in a restrictive manner) to use a fibroscope (or similar object) in association with the device of the present invention: by inserting the fibroscope, the curvature is temporarily "straightened up" (because the fibroscope in an advanced position touches the tip on the "inner" side) while by exerting pressure beyond the fibroscope, the fibroscope will cause the tip of device 1 to be moved out of its way (so that the device 1 is straightened up).

Due to this interaction of mechanical interference between fibroscope and sheath, it is conveniently possible to insert everything and, as soon as the desired point is reached, identification of the perforation area is made possible by localising the position of the light emitted by the fibroscope (that is lighting the operation area from the inside).

After this identification has been carried out, the fibroscope can be retracted by an amount sufficient to make the tip become curved again, which tip in turn, as provided, will touch the wall to be perforated so that the operation can begin.

It is to be pointed out that in a first case, the fitting means 4 can consist of a wire connected to the second end 7b of the secondary channel 7 that, suitably pulled towards the first end 7a, tends to promote bending, or alternatively said means can consist of thermo-shrinkable materials to be activated by electric currents (the so-called electro-active materials), or other systems suitable for the purpose.

In a first embodiment shown in FIG. 4, spout 9 substantially is of truncated conical shape (or at all events of a shape similar to that of a cone), tapering towards the second end 7b of the secondary channel 7, and acts as a dilator body of the stoma created by the perforation element 5. In this case the perforation element 5 comprises a wire 5a to an end of which a needle 5b is connected. The wire 5a has a body 5c interfering with an inner section of the secondary channel 7.

After inserting a tracheoscope or an endoscope inside the device 1, in particular inside the main channel 6 of sheath 2, the whole is inserted into the trachea of a patient (or also, depending on current requirements, into an endotracheal cannula); with the aid of the optical probe of the fitting means 4 the device is positioned until the exact perforation point is reached.

The operator slides the perforation element 5 into the secondary channel 7 being guided by spout 9 to the perforation point. Once the perforation element 5 and therefore needle 5b, has perforated the trachea emerging to the outside, the surgeon pulls the wire until the interfering body 5c abuts against an inner narrowing of the secondary channel 7. Starting from this moment the perforation element 5 also acts as a traction element: the wire 5a pulled by the surgeon, drags along the sheath 2 therewith. The cone-shaped spout 9, following wire 5a enters the formed hole and progressively dilates it. After the trachea has been perforated, the endoscope or at all events the fitting means can be removed.

Figure 6:
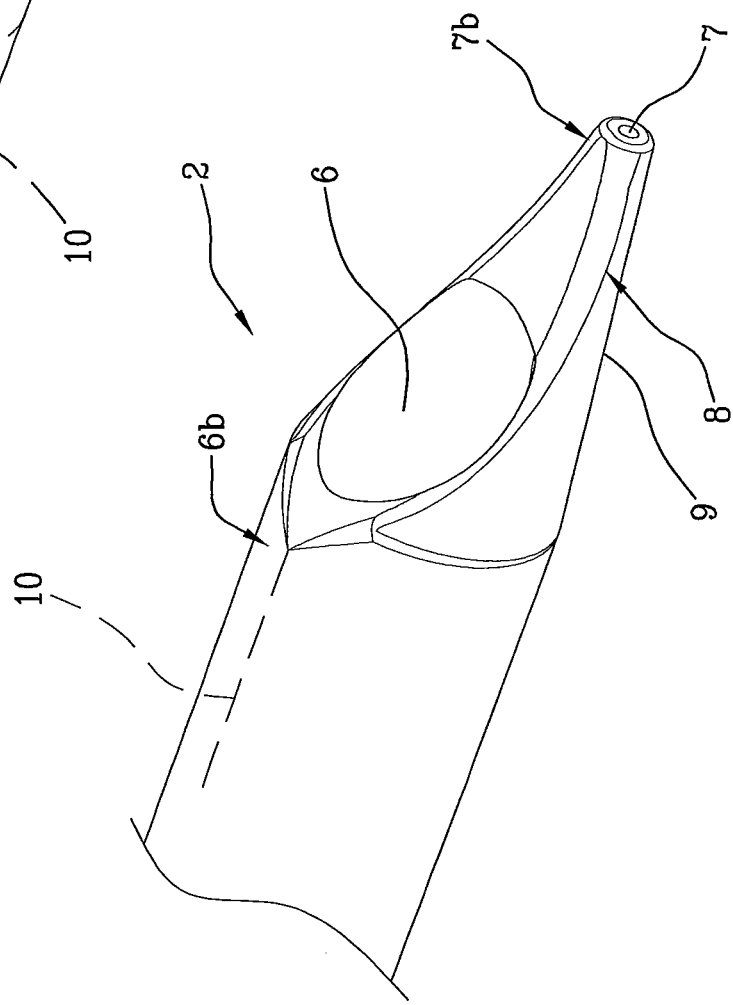
FIG. 6 is a perspective view of a portion of the device in FIG. 1 with a second example of a construction detail.

Sheath 2 has weakening and/or frangible lines 10 in the vicinity of the second end 7b of the main channel 6, as shown in FIGS. 5 and 6. These weakening lines 10 can be made longitudinally, and therefore parallel to the axis 2a of sheath 2, and/or transversely relative to this axis 2a.

Depending on current requirements it is also possible for the weakening and/or frangible lines to be only traced on sheath 2, so that the operator can visually identify them and thus know where the necessary incisions are to be made. These weakening lines 10 are particularly useful in the first embodiment just described and illustrated in FIG. 1. In fact, once sheath 2 partly emerges from the stoma towards the outside, and therefore is placed partly inside the trachea and partly at the outside, the second end 6b, 7b of both channels is cut. A ventilation tube or tracheoscope of known type and therefore not illustrated, is inserted into the main channel 6 and it will be placed within the trachea to allow the patient to breathe. The weakening lines 10 enable the ventilation tube to pierce sheath 2 and be routed along the trachea. At this point the disposable sheath 2 can be removed and definitive positioning of the ventilation tube can be carried out, as well as final connection of same to a breathing machine or another useful apparatus, depending on current requirements.

In a second embodiment shown in FIG. 3 a spout 9 in the shape of a flute spout can be provided. As shown in FIG. 4, spout 9 in this second configuration has an exit section of the perforation element 5 that is larger than the corresponding exit section of the previously described embodiment shown in FIG. 2.

The perforation element 5 associated with this device in fact has a larger body: in particular, in this case, the perforation element 5 comprises a needle 5b connected to a ventilation cannula 5d through a wire 5a and a dilator body 5e. Alternatively, needle 5b can be connected to an "inner sheath" 5d the function of which is to prevent the so-called "false ways" to be taken during the perforation step (or in other words, during introduction from the outside to the inside). In other words, needle 5b is connected to wire 5a which is connected to the tip of a cone-shaped dilator body 5a, to the base of which a cannula or ventilation tube 5d is attached. This cannula 5d is preferably made of an elastically deformable material.

Use of device 1, in accordance with this second embodiment, is the same as that previously described. The only difference resides in that in this case spout 9 exclusively acts as a guide and not also as a retractor element. In fact, once device 1 has been positioned within the trachea and the stoma has been created, the surgeon pulls the wire 5a so that the dilator body 5a enters the stoma and gradually dilates it. Then the surgeon goes on pulling the wire and fully extracts the dilator body 5e until also part of the ventilation cannula 5d emerges externally of the stoma.

At this point the surgeon takes the whole device 1 out of the mouth and terminates the correct positioning of the ventilation cannula 5d cutting the wire and the dilator body 5e and connecting the cannula to a breathing machine (or introducing the ventilation cannula into the inner sheath 5d). Advantageously, along the secondary channel 7 weakening lines 10 can be present that, due to breaking during passage of the breaking element, make advancing of the cannula easier.

Advantageously, the device for tracheotomy being the object of the present invention can be provided in a kit for tracheotomy comprising an endoscope or a tracheoscope equipped with an optical probe and a lighting device, and a perforation element in accordance with either of the two embodiments previously described.

The invention achieves important advantages.

In fact, the tracheotomy device of the invention allows the stoma to be obtained from the inside to the outside, thus avoiding the drawbacks found in the known art.

The device enables perforation and introduction of the ventilation cannula with a smaller number of manoeuvres and in a simpler manner as compared with the known art.

The sheath put on the endoscope or the tracheoscope is disposable and therefore ensures the maximum degree of hygiene and disinfection. In addition, selection of the materials and/or conformation made possible by the present structure of the device allows the trachea anatomy to be better followed, so that the operation is less damaging to the patient and allows more safe conditions to be adopted.

Finally, it is possible to see that the perforation element is introduced and guided within the secondary channel in such a manner that it is closely in contact with the endoscope, so that any operation is facilitated.

The invention claimed is:

1. A tracheotomy device comprising a perforation element, fitting means carrying endoscopic surgical instruments insertable in a trachea, a disposable flexible sheath to be put on said fitting means; said sheath comprising a main channel for insertion of said fitting means and a secondary channel for insertion of said perforation element slidably movable inside the secondary channel, wherein:
the tracheotomy device comprises guide and pointing means for guiding the perforation element in a perforation direction;
said guide and pointing means in the perforation direction comprising a spout;
said spout is an end portion of said secondary channel;
said spout being a dilator body and is tapered towards the second end of said secondary channel;
said perforation element having a needle which contains a means to drag the spout;
said means to drag the spout being an interfering body connected to said needle through a wire and interfering with an inner narrowing of an inner section of said secondary channel, whereby on pulling said wire said spout is dragged by means of the interference between said body and said narrowing.

2. A tracheotomy device as claimed in claim 1, wherein said main channel and secondary channel both have a first end that is open and through which the fitting means carrying the endoscopic instruments and the perforation element are respectively inserted, and a second end that is open and through which the fitting means carrying the endoscopic instruments and the perforation element respectively emerge.

3. A device as claimed in claim 1, wherein said secondary channel has stiffening ribs distributed along its longitudinal extension which are designed to counteract deviations of the perforation element.

4. A device as claimed in claim 1, wherein said spout is a portion of the secondary channel exceeding said main channel in length.

5. A device as claimed in claim 1, wherein said spout has a curvature the concavity of which faces a longitudinal axis of the sheath.

6. A device as claimed in claim 1, wherein said spout has a preformed curvature.

7. A device as claimed in claim 6, wherein the curvature of said spout is obtained through bending-controlling means.

8. A device as claimed in claim 1, wherein said main channel and secondary channel both have a first end that is open and through which the fitting means carrying the endoscopic instruments and the perforation element are respectively inserted, and a second end that is open and through which the fitting means carrying the endoscopic instruments and the perforation element respectively emerge.

9. A device as claimed in claim 1, wherein said sheath has weakening and frangible lines in the vicinity of the second end of said main channel or along said secondary channel.

10. A device as claimed in claim 9, wherein said weakening and frangible lines are disposed longitudinally or transversely of an axis of said main channel.

11. A device as claimed in claim 1, wherein said perforation element is also a traction element.

12. A kit for tracheotomy comprising a device as claimed in claim 1, an endoscope insertable in said device and a perforation element insertable in said device.

13. A device as claimed in claim 1, wherein the spout is curved.

14. A device as claimed in claim 1, wherein the spout is susceptible of bending.

* * * * *